(12) United States Patent
Hasegawa et al.

(10) Patent No.: US 10,786,173 B2
(45) Date of Patent: Sep. 29, 2020

(54) SIMILARITY EVALUATION METHOD USING BRAIN WAVES, EVALUATION DEVICE, EVALUATION SYSTEM, AND PROGRAM

(71) Applicant: National Institute of Advanced Industrial Science and Technology, Tokyo (JP)

(72) Inventors: Ryohei Hasegawa, Ibaraki (JP); Tomomi Fujimura, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 67 days.

(21) Appl. No.: 15/527,144

(22) PCT Filed: Nov. 16, 2015

(86) PCT No.: PCT/JP2015/082101
§ 371 (c)(1),
(2) Date: May 16, 2017

(87) PCT Pub. No.: WO2016/080341
PCT Pub. Date: May 26, 2016

(65) Prior Publication Data
US 2017/0340230 A1    Nov. 30, 2017

(30) Foreign Application Priority Data

Nov. 17, 2014    (JP) .................... 2014-232786

(51) Int. Cl.
*A61B 5/0484*    (2006.01)
*G06Q 30/02*    (2012.01)
(Continued)

(52) U.S. Cl.
CPC ........ *A61B 5/0484* (2013.01); *A61B 5/04012* (2013.01); *A61B 5/0478* (2013.01);
(Continued)

(58) Field of Classification Search
CPC .... A61B 5/0484–04847; A61B 5/7264; A61B 5/04012–04018; A61B 2503/12;
(Continued)

(56) References Cited

U.S. PATENT DOCUMENTS

2009/0318775 A1* 12/2009 Michelson ............. G06Q 10/00
                                                          600/301
2010/0274035 A1    10/2010 Muller et al.
(Continued)

FOREIGN PATENT DOCUMENTS

JP            S5799945 A     6/1982
JP            2000254239 A   9/2000
(Continued)

OTHER PUBLICATIONS

International Search Report, PCT/JP2015/082101, dated Feb. 2, 2016, pp. 3.
JP2010-274035 A; National Institute of Advanced Industrial Science and Technology, Dec. 9, 2010, paragraphs [0010], [0012], [0017], to [0020], [0022] and [0027] with English Abstract & Partial Machine translation.
Samuel M. McClure et al, "Neural Correlates of Behavioral Preference for Culturally Familiar Drinks", Neuron, vol. 44, 379-387, Oct. 14, 2004.

*Primary Examiner* — Catherine B Kuhlman
(74) *Attorney, Agent, or Firm* — Cantor Colburn LLP

(57) ABSTRACT

Provided are a method, a device, a system, and a program for evaluating similarity of brain activity with respect to an object to be evaluated, using data obtained by a simple measurement of brain waves. Brain wave data related to cognitive processing with respect to a plurality of sensory stimuli are dimensionally compressed, and a distribution of the object to be evaluated is displayed on a two-dimensional plane or three-dimensionally. In this way, similarity of brain information with respect to the plurality of sensory stimuli is evaluated, and the similarity is visualized. The brain wave (Continued)

data related to the cognitive processing include brain wave data upon selection of a stimulus as a target, and brain wave data caused by a non-target stimulus event.

5 Claims, 4 Drawing Sheets

(51) Int. Cl.
*A61B 5/00* (2006.01)
*A61B 5/04* (2006.01)
*G16H 10/60* (2018.01)
*A61B 5/0478* (2006.01)
*G16H 10/20* (2018.01)

(52) U.S. Cl.
CPC ............ *A61B 5/7264* (2013.01); *G06Q 30/02* (2013.01); *G16H 10/60* (2018.01); *A61B 5/04842* (2013.01); *A61B 2503/12* (2013.01); *G06Q 30/0201* (2013.01); *G16H 10/20* (2018.01)

(58) Field of Classification Search
CPC ......... G06Q 30/02–0284; G16H 10/20; G16H 10/60
See application file for complete search history.

(56) References Cited

U.S. PATENT DOCUMENTS

| 2012/0101401 A1* | 4/2012 | Faul ..................... A61B 5/0476 600/544 |
| 2013/0128701 A1 | 5/2013 | Derkx et al. |
| 2015/0026195 A1* | 1/2015 | Hasegawa ............ A61B 5/0476 707/748 |

FOREIGN PATENT DOCUMENTS

| JP | 2004342119 A | | 12/2004 | |
| JP | 2007125362 A | | 5/2007 | |
| JP | 2010274035 A | * | 12/2010 | |
| JP | 2010274035 A | | 12/2010 | |
| JP | 2011104340 A | | 6/2011 | |
| JP | 2012053656 A1 | | 3/2012 | |
| JP | 2012073329 A | | 4/2012 | |
| JP | 2013178601 A | | 9/2013 | |
| WO | WO-2013128701 A1 | * | 9/2013 | ........... A61B 5/0476 |
| WO | 2016080341 A1 | | 2/2016 | |

\* cited by examiner

Reaction of brain wave

Elapse of time

| | Test stimulus | | | |
|---|---|---|---|---|
| | 🍌 | 🍇 | 🍎 | 🍊 |
| 🍌 | 4 | -3 | -5 | -4 |
| 🍇 | -5 | 3 | -1 | -2 |
| 🍎 | -3 | -4 | 6 | 3 |
| 🍊 | -6 | -5 | 2 | 5 |

(Target on left axis)

(A) Theoretical value (B) Measured value

SIMILARITY EVALUATION METHOD USING BRAIN WAVES, EVALUATION DEVICE, EVALUATION SYSTEM, AND PROGRAM

TECHNICAL FIELD

The present invention relates to a method, an evaluation device, an evaluation system, and a program for visualizing and evaluating brain information concerning similarity evaluation with respect to a plurality of stimuli.

BACKGROUND ART

Conventional questionnaire surveys, which are one of the primary means of market research conducted for product development, sales strategy and the like, often suffer from accuracy or reliability problem in the survey results due to conscious or unconscious bias of the respondents. In recent years, there have been major efforts to analyze brain activities related to consumer behavior and develop marketing research methods based on brain activity. For example, researches are known that, by brain activity measuring experiments using large equipment referred to as fMRI, attempted to identify brain locations associated with preferences and brand consciousness, and to investigate differences in brain activity caused by the strength of brand (see Non Patent Literature 1). Lately, corporations have started neuromarketing focusing on brain waves (a sensibility evaluation technique based on brain information).

The conventional techniques focusing on brain waves have attempted to interpret brain waves by investigating the correlation between the results of rating of the questionnaire by a question sheet with respect to various emotion types, such as pleasant and unpleasant, and the brain waves. With this technique, the intensity of each emotion can be estimated to some extent from the brain waves when the brain waves and the emotion types have a high correlation. However, the technique suffers from a decrease in the probability of making correct estimations of the emotions from the brain waves when the correlation is low. In addition, the technique employs the logic that says, based on a database of a number of subjects, "Generally, when such brain waves are observed, the associated emotion state is this". This, however, disregards the fact that the brain wave pattern, even in a normal range, has variations from one subject to another, making it doubtful whether scientifically meaningful data analysis is being made. Indeed, the significance of drawing from the brain waves information that can be learned from the question sheet is unclear.

A research group for the present invention has carried out research and development concerning brain information analysis techniques for sensibility evaluation from which the subjective bias of the subject can be eliminated as much as possible. As one outcome, the group has proposed a dimensional compression technique based on differences in brain wave reactions (potential-change amplitude data) to a simple successive presentation of various stimuli (see Patent Literature 1). Patent Literature 1 proposes a display method for visualizing brain information. The method is characterized in that multi-channel brain wave data obtained from a plurality of measurement locations with respect to a plurality of feeling stimuli (including linguistic stimuli) are dimensionally compressed, and a stimulus distribution is displayed on a two-dimensional plane to show that stimuli at a small distance are associated with more similar brain activities than stimuli at a large distance.

The present inventors have also developed intension transmission assistance devices and methods for transmitting intensions by brain activity analysis (see Patent Literatures 2 and 3). Patent Literature 2 proposes determining that a specific decision has been made in the brain based on a discrimination function obtained by analyzing brain wave data provided by measuring a brain wave after stimulus presentation, and a success rate. Patent Literature 3 proposes an intension transmission assistance technique using a combination of messages. According to the technique, brain wave data after stimulus presentation are analyzed, and, using a function for estimating an intra-brain processing sequence related to a decision for each trial of "a message constituent element" which is a cognitive task, it is determined that a specific decision has been made in the brain. The techniques according to Patent Literatures 2 and 3 can assist intension transmission for, e.g., a motion-impaired person having difficulty speaking or writing, or a severely motion-impaired person having difficulty performing input operations for various devices using hands or legs.

The present inventors have also proposed a device and a method for ordering objects under investigation based on brain wave analysis (see Patent Literature 4).

CITATION LIST

Patent Literature

Patent Literature 1: JP 2010-274035 A
Patent Literature 2: JP 2012-053656 A
Patent Literature 3: JP 2012-073329 A
Patent Literature 4: JP 2013-178601 A

Non Patent Literature

Non Patent Literature 1: McClure S M, Li J, Tomlin D, Cypert K S, Monyague L M, Montague P R. "Neural Correlates of Behavioral Preference for Culturally Familiar Drinks" Neuron 44, pp. 379-387, 2004

SUMMARY OF INVENTION

Technical Problem

A marketing research method requires an index which enables prediction of consumer behavior by more directly identifying the thought and sensibility of a respondent using a method that is not affected by the respondent's conscious or unconscious bias. Implementation of a conventional marketing research method based on brain activity that may be promising in this respect has had the following problem. The method that examines brain activity using a device such as functional MRI (fMRI) requires a large experimental facility. In addition, the subject has to suffer the discomfort of having to have his or her head held in the fMRI device for measurement, and the device needs to be specially adapted to present the product under investigation. On the other hand, the measuring of scalp brain waves does not require any invasive operation, and enables simple measurement of brain activity without using a large experimental facility. However, since the detailed relationships between data obtained by brain activity measurement and subject behaviors are not known, it has been difficult to decode concrete in-brain information from brain wave activity patterns.

The analysis method the present inventors have proposed in Patent Literature 1 is directed to the brain information when the subject is passively receiving a stimulus. The analysis method does not evaluate the brain information when the subject actively receiving a stimulus.

The present inventors have conducted researches aimed at evaluating the brain information when the subject is actively receiving a stimulus.

The present inventors have constructed a system for acquiring brain wave data including the brain information at the time of actively receiving a stimulus, using a cognitive task that requires discriminating one of a plurality of kinds of stimulus presented to the subject (a cognitive task that requires making a decision as to whether to "select" or "not select" in the head. As an initial attempt with respect to such brain wave data, the present inventors have developed a system whereby the intensities of brain wave reactions when each stimulus to be considered is distinguished and selected over other stimuli in the brain are compared, using an index of the results of discrimination analysis and the like, and unambiguously ordered (see Patent Literature 4).

The present inventors contemplated that the system of Patent Literature 4 would provide a robust tool for evaluating brain information having reduced subjective bias including the activity of subconscious mind. However, the analysis results are limited to the identification of the stimulus provoking the strongest "degree of interest in the brain", or to one-dimensional quantitative data (which may be interpreted as order data). Accordingly, the technique of Patent Literature 4 is unable to provide a map-like overview of the similarity of all stimuli, as in Patent Literature 1. Furthermore, the technique of Patent Literature 4 is limited to brain information with respect to the brain wave data at the time of "having selected", and the brain information that is included in the brain wave data at the time of "having not selected" remains un-utilized.

The present invention is aimed at solving the above problems, and an object of the present invention is to provide a device, a method, a system, and a program for evaluating stimulus similarity based on brain waves, using data obtained by simple measurement of brain waves. Another object of the present invention is to visualize in-brain information.

Solution to Problem

In order to achieve the objects, the present invention includes the following features.

An evaluation method according to the present invention for evaluating similarity of brain information with respect to a plurality of sensory stimuli includes dimensionally compressing brain wave data related to cognitive processing with respect to the plurality of sensory stimuli, and displaying a distribution of the stimuli on a two-dimensional plane or three-dimensionally. The brain wave data related to the cognitive processing may include brain wave data upon selection of a stimulus as a target, and brain wave data caused by a non-target stimulus event. The dimensional compression may be based on a combination of multivariate analysis methods.

A brain information similarity evaluation device according to the present invention includes a stimulus presentation means; a brain wave measurement means; and an evaluation processing means which evaluates stimulus similarity based on brain wave data. The stimulus presentation means presents a plurality of sensory stimuli as a plurality of stimulus events including a target and a non-target, each a plurality of times. The brain wave measurement means measures brain waves immediately after the stimulus presentation by the stimulus presentation means. The evaluation processing means subjects the brain wave data, while a cognitive task with respect to the plurality of sensory stimuli is being undertaken, to dimensional compression based on a combination of multivariate analysis methods, and displays points corresponding to the stimuli on a two-dimensional plane or three-dimensionally.

According to a brain information similarity evaluation system of the present invention, brain wave data are obtained by measuring a brain wave related to cognitive processing with respect to a plurality of sensory stimuli, the brain wave data are subjected to dimensional compression based on a combination of multivariate analysis methods, and points corresponding to the stimuli are displayed on a two-dimensional plane or three-dimensionally.

A program according to the present invention is a program for causing a computer to function as: a stimulus presentation means which presents a plurality of sensory stimuli as a plurality of stimulus events including a target and a non-target, each a plurality of times; an evaluation processing means which evaluates stimulus similarity based on brain wave data, the evaluation processing means subjecting brain wave data, while a cognitive task with respect to a plurality of sensory stimuli presented by the stimulus presentation means is being undertaken, to dimensional compression based on a plurality of multivariate analyses methods, and displaying points corresponding to the stimuli on a two-dimensional plane or three-dimensionally; and a presentation means which presents an evaluation result.

Advantageous Effects of Invention

According to the present invention, the brain information is also evaluated during the execution of a cognitive task, i.e., when the subject is actively receiving a stimulus. Accordingly, a highly reliable result can be obtained. According to the present invention, brain wave data associated with the cognitive processing are dimensionally compressed, and a distribution of the stimuli is displayed on a two-dimensional plane, whereby it can be displayed that the stimuli at a small distance have similar brain activities compared with the stimuli at a large distance. That is, based on the stimulus-to-stimulus distance being displayed, the similarity of in-brain information with respect to stimuli can be evaluated.

According to the present invention, the subject's brain activity is measured noninvasively using brain waves, so that the information in the brain can be simply visualized. In addition, because the brain activity is directly measured, higher reliability can be achieved than is possible with a questionnaire survey which is subject to conscious biasing. Because the brain activity is directly measured, it is possible to visualize unconscious impressions, sensibility information and the like, which are difficult to measure by conventional questionnaire surveys. The data of brain activities that have conventionally been too complex to be rendered into meaning are two-dimensionally displayed by analyzing the brain wave data while a cognitive task is being undertaken, and by performing dimensional compression from a multi-dimension. When displayed two-dimensionally, it can be learned that objects having a small distance on a map are being determined to be similar in the brain, and that objects at a distance are being determined to be different in the brain. In this way, the information in the brain can be visualized. In addition, because averaged data for each group of subjects can be visualized, the present invention may be used for marketing research for new product development in place of a questionnaire survey.

DESCRIPTION OF EMBODIMENTS

Figure 1:
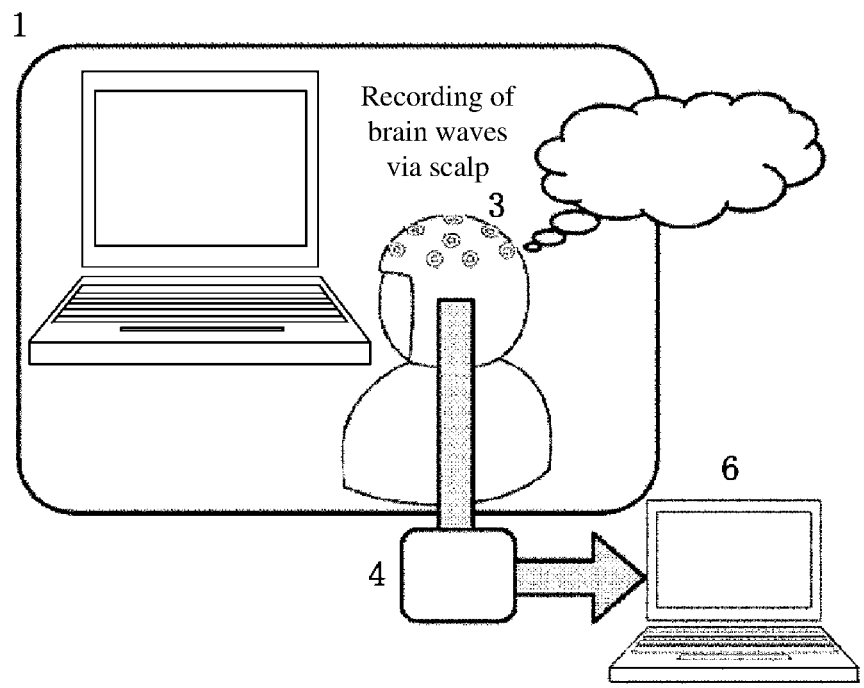
FIG. 1 is a schematic diagram of a device according to the present invention.

An embodiment of the present invention will be described.

According to the embodiment of the present invention, brain waves are analyzed to enable visualization of brain information concerning similarity evaluation with respect to a plurality of stimuli. More specifically, the embodiment of the present invention relates to a technique for visualizing, as a low-dimension structure, brain information with respect to the similarity of a plurality of stimuli (visual stimuli, such as a commercial product), by performing multivariate analysis on the brain wave data of multi-channels and the like noninvasively measured from the scalp.

As described above, because the technique of Patent Literature 4 is limited to the brain information with respect to the brain wave data at the time of "having selected", the brain information included in the brain wave data at the time of "not having selected" remains un-utilized. The present inventors have developed the present invention by focusing on the possible inclusion of information of similarity to the "selected" stimulus by analyzing the feature of the brain wave data at the time of "not having selected".

According to the embodiment of the present invention, in comparing a plurality of stimuli, a dimensional compression technique which is useful in identifying the overall picture of similarity rather than ordering is used to visualize brain information with respect to the data of both "when selecting" and "when not selecting", whereby a stimulus similarity evaluation system using brain waves is provided, as described in the following.

That is, the embodiment of the present invention provides a system which enables visualization of brain information concerning similarity evaluation with respect to a plurality of stimuli, the brain information being included in brain wave data associated with cognitive processing. Herein, the brain wave data associated with cognitive processing, or the brain wave data related to cognitive processing, with respect to a plurality of sensory stimuli, refer to brain waves generated when a target sensory stimulus is counted among successively presented sensory stimuli. As visualization means, a plurality of multivariate analyses is used. The plurality of multivariate analyses involves, focusing on scores that can be referenced as the result of pattern identification such as discrimination analysis, visualization in a low-dimension space by a dimensional compression technique, such as multidimensional scaling. An example of a multivariate analyses combination is a technique whereby, focusing on scores that can be referenced as the result of pattern identification such as discrimination analysis, stimuli are allocated into similar groups by cluster analysis. In this case, if a physical feature is computed, correspondence or no-correspondence with a theoretical value (such as an annular arrangement illustrated in the embodiment) can be evaluated.

The "brain information map" according to the conventional art of Patent Literature 1, because it focuses on reactions to visually evoked potentials with respect to (of) passive stimulus presentations that do not require cognitive processing (when no cognitive task is even being undertaken), leads to a "map" reflecting differences (similarities) in physical characteristics. On the other hand, according to the embodiment of the present invention, it is believed that because attention is focused on the brain waves (event-related potential) reflecting the cognitive processing when the subject is actively paying attention, a distribution chart results which mainly reflects subjective differences (similarities).

In addition, in the data analysis according to the conventional technique of Patent Literature 1, all of passively presented stimuli are equally handled and analyzed. On the other hand, in the embodiment, data are separated for each game of cognitive task. Handling of data includes a method by which only the data with respect to a target stimulus in each game are collected, and a method by which target and other (average of all non-targets) data are handled. In the embodiment, while data are grouped for each game, not only the target but also non-targets are handled, and all kinds of data are equally handled in a group without making a distinction between the target and the non-target. In this way, when a certain stimulus is made a target, a variation in a non-target for which the reaction is slightly increased by being mistaken for the target is also considered an object of analysis as similarity data. By handling such variation characteristics for the data of games with different targets, it becomes possible to efficiently obtain similarity data between stimulus types in a multifaceted manner.

According to the embodiment of the present invention, focusing on brain activity, in particular a brain wave component (event-related potential) that can be recorded on the scalp and that reflects cognitive processing evoked by a stimulus input, the brain reactivity with respect to a presentation of a plurality of stimulus events is analyzed to evaluate the similarity of a plurality of stimulus events. The event-related potential on which the present invention focuses is a transient brain wave, such as P300 (a positive potential change which becomes stronger 300 milliseconds after stimulus presentation), caused in conjunction with the timing of occurrence of an external or internal event. Examples of the stimulus event include physical sensory stimuli (sensory stimuli of the senses of, e.g., sight, hearing, smelling, tasting, and touching) concerning a plurality of objects to be evaluated, and linguistic stimuli. In the present invention, the physical sensory stimuli (the sensory stimuli of the senses of, e.g., sight, hearing, smelling, tasting, and touching) and linguistic stimuli are collectively referred to as sensory stimuli. The present invention, specifically, mainly includes the elements of stimulus event presentation, brain wave measurement, evaluation processing by brain wave data analysis, and evaluation result presentation. More specifically, a device according to the embodiment of the present invention is provided with a brain wave measurement headgear, a data analysis computer, and a stimulus presentation device (for example, a display screen).

First Embodiment

The embodiment will be described with reference to the drawings. FIG. 1 schematically illustrates the device and method according to the embodiment. As illustrated in FIG. 1, in stimulus presentation 1 to the subject, the subject is shown a display screen for stimulus presentation, and the scalp brain waves of the subject are measured and recorded by an electroencephalograph (a brain wave amplifier 4 in the figure). The subject is fitted with electroencephalograph electrodes 3 on the head for measuring brain waves. For example, a head-mounted device on which the electroencephalograph electrodes are affixed is used. Various visual stimuli are presented on the display screen (monitor), and data of a raw waveform of brain waves are obtained by the electroencephalograph. The data of the brain wave raw waveform are analyzed and processed by a processing device, such as a computer 6, and the results of evaluation of in-brain information of stimulus similarity are displayed on the display screen and the like. In FIG. 1, the thick arrow extending from the head fitted with the brain wave electrodes to the brain wave amplifier 4, and from the brain wave amplifier 4 to the computer 6 schematically illustrates the transmission of signals via wires or wirelessly.

Figure 2:
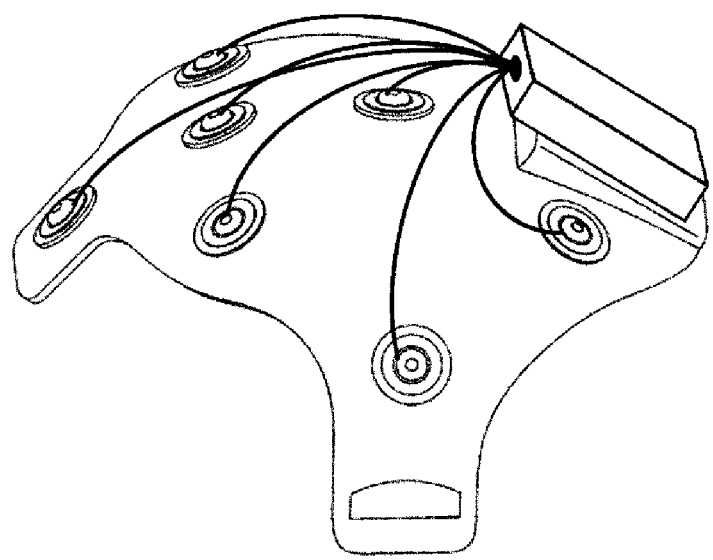
FIG. 2 is a schematic diagram illustrating a brain wave measurement device according to a first embodiment.

FIG. 2 illustrates an example of the head-mounted member (headgear) on which the electroencephalograph electrodes used in the embodiment are affixed. The headgear is provided with brain wave measurement electrodes fixedly held on the headgear; wiring electrically connecting the electrodes with an electroencephalograph body portion; and a wireless transmission unit for transmitting the measured brain wave data.

In the embodiment, brain waves from one or a plurality of electrodes attached to the scalp are measured, centered around the top of the head, which is effective for measuring brain waves reflecting an increase in attention.

Figures 3, 4:
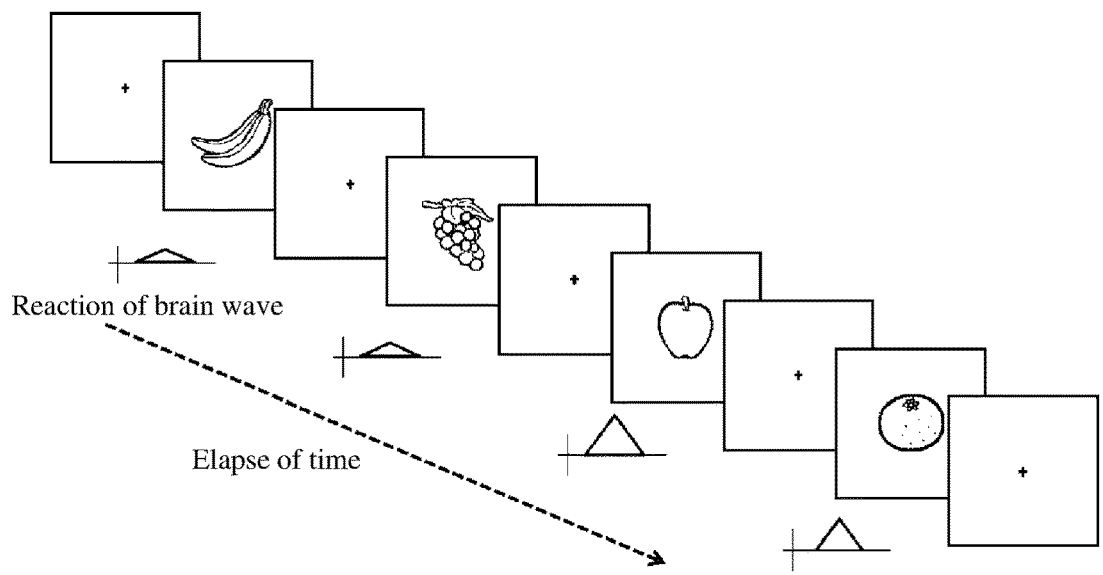
FIG. 3 is a schematic illustration of a stimulus presentation means and brain wave data according to the first embodiment.
FIG. 4 is a diagram for illustrating the first embodiment, showing brain wave intensities by discrimination scores.

FIG. 3 schematically illustrates the presentation of stimulus events and the reaction of the subject's brain waves thereto over time according to the embodiment. As illustrated in FIG. 3, the subject is presented with stimulus events (which may be referred to as attention evoking events or test stimulus events), such as simple figures, one event (1 sheet) at a time. The brain waves of the subject who watched the figures are measured by the electroencephalograph with the electrodes attached to the subject's head, and the brain waves are analyzed by a brain wave analysis processing device, such as a computer.

The stimulus events may include signs, illustrations, picture, and photographs. At the bottom of FIG. 3, in order to describe the present embodiment, there are schematically shown brain waves corresponding to the plurality of stimulus events, the stimulus events varying over time. Specifically, (a) stimulus event presentation and brain wave measurement with respect to the stimulus events, and (b) stimulus similarity evaluation processing based on brain wave data are implemented as follows. Display processing for visualizing the evaluation processing results in the form of a diagram and the like may be provided as appropriate.

(a) Stimulus Event Presentation and Brain Wave Measurement with Respect to the Stimulus Event The subject is presented with one of a plurality of stimulus events concerning various objects for which similarity is to be evaluated, such as eight figures, as a "target". A cognitive task of counting in the head the number of times a target stimulus event is presented among the successively presented stimulus events is implemented for each subject, and the corresponding brain waves are measured. The brain waves are measured from one or a plurality of electrodes attached to the scalp centered around the top of the head. The measurement is performed by the following procedure.

(1) The subject is presented with the visual stimuli concerning a plurality of objects to be evaluated (visual stimuli such as photographs or illustrations of products). For example, the visual stimuli (pictures of fruits in FIG. 3) are successively presented, like a picture-story show, on a computer display screen and the like in a pseudo-random sequence (see FIG. 3). In the case of sensory stimuli of the senses of, e.g., hearing, smelling, tasting, and touching instead of visual stimuli, the stimuli are also similarly presented over time.

(2) One of the plurality of visual stimuli (which comprise a plurality of pictures of fruits in FIG. 3) is defined as the "target", and the other stimuli are collectively referred to as the "non-target". While the target and the non-target are repeatedly presented in a pseudo-random manner, the subject is asked to count in the head the number each time the target is presented. In the present invention, the trial of successive stimulus presentation for detection of a certain specific target is collectively referred to as a "game".

(3) After a short rest, another game, i.e., the above (2), is executed, with the presentation of the target stimulus event being changed in sequence. This is repeated until all of the plurality of visual stimuli are implemented as targets. For example, when eight kinds of visual stimuli (fruits) are used, a total of eight games are implemented. By thus performing the games with the successively changed target, all stimuli are presented as targets. Normally, when there are eight types of stimuli, there are eight games to be implemented, and all of the games (one session) are performed.

The above (2) and (3) will be described in greater detail. For example, with respect to all of the types of targets of banana as the first target; grape as the second target; apple as the third target; and orange as the fourth target, brain wave data in the case of the target and brain wave data in the case of non-target are obtained. The brain wave data illustrated in the bottom of FIG. 3 are examples of the brain wave data corresponding to the respective visual stimuli when the subject, having been taught that the target was the apple, was asked to count while being shown the visual stimuli. As schematically illustrated in FIG. 3, the brain wave data with respect to the target visual stimulus (apple), the brain wave reaction was larger compared with the brain wave data with respect to the non-target visual stimuli (banana, grape, and orange). Similarly, when the other targets were taught, the brain wave data with respect to the target visual stimuli among the brain wave data indicated in many cases greater brain wave reactions than the brain wave data with respect to the non-target test stimuli.

(b) Evaluation Processing of Stimulus Similarity Based on Brain Wave Data (1) After the end of session (a) of brain wave measurement, with respect to the brain wave data during the execution of task, a model formula (which is set such that the discrimination score with respect to the target becomes high) for distinguishing the target and the non-target is generated, using a pattern identification technique (such as linear discrimination analysis), and a discrimination score with respect to each stimulus immediately after the presentation thereof is calculated. In this case, in order to avoid an overlap of model data and data for prediction, cross validation is used.

FIG. 4 shows, in table form, the discrimination scores of brain wave data with respect to the respective test stimuli in the case where the targets are the stimulus types shown in the left column of the figure, using four stimulus types as a simple example. For example, the first row shows that, when the target is banana, the discrimination score with respect to the stimulus event of banana is 4; the discrimination score with respect to the stimulus event of grape is −3; the discrimination score with respect to the stimulus event of apple is −5; and the discrimination score with respect to the stimulus event of orange is −4.

(2) The obtained discrimination scores are averaged for each stimulus type (including both the target and the non-target). Based on a data arrangement (stimulus types×number of games) in which the averaged results are compiled, a triangular matrix is computed which indicates the difference in discrimination scores between the stimuli in terms of Euclidean distance.

Figure 5:
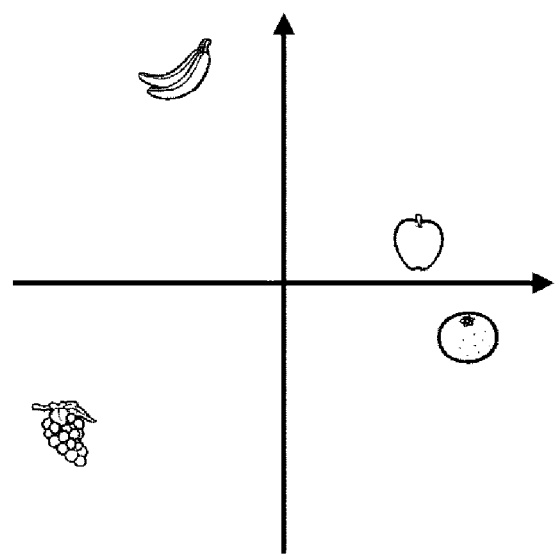
FIG. 5 illustrates the results of similarity evaluation by the brain wave data discrimination scores according to the first embodiment.

(3) Based on the triangular matrix obtained by computing, multivariate analysis (such as multidimensional scaling or principal component analysis) is applied to plot the respective stimulus types on two-dimensional or three-dimensional coordinates. FIG. 5 illustrates a plot of the similarity evaluation results.

In the following, a detailed description will be provided using mathematical expressions.

(b-1) Division of Data for Discrimination Model Formula Generation

In the embodiment, after data are divided by means of cross validation as follows, a discrimination model formula is generated and the success or failure of target decoding is determined. First, a discrimination model formula is created from the brain wave data in the case where test stimuli are presented as a target or a non-target in games (the second to the eighth games) other than the particular game for determining the decoding success or failure (the first game, for example). Thereafter, with respect to each of the stimulus events in the particular game (the first game), a discrimination score is calculated to make the decoding success or failure determination. For the decoding success or failure determination for another game (such as the second game), a discrimination model formula generated from the data of all of the remaining games (the first and the third to the eighth games) other than the game is used. In this way, the data for discrimination are eliminated from the process generating the model formula, whereby over-evaluation in the decoding success or failure determination can be avoided. Even when cross validation is used, the discrimination model formula can be interpreted to be appropriate if the decoding accuracy based on in what game of all of the games the decoding was successful is sufficiently high.

(b-2) Method for Determining Discrimination Scores

For example, a discrimination score (y) with respect to a single presentation of each image (visual stimulus) is calculated using a linear discrimination function expressed by the following formula.

$$y = \sum_{i}^{n} w_i x_i + c \qquad \text{(Expression 1)}$$

In the expression of y, x is the value of brain wave data (voltage) of a certain channel at a certain point in time. The value x has types (n) corresponding to the product of the number of channels (the number of channels corresponding to the number of measurement locations because the brain wave data are obtained at a plurality of measurement locations on the scalp of the subject's head) and the data points. The weighting coefficient w with respect to the respective brain wave data and the constant term c can be determined by linear discrimination analysis.

A cumulative discrimination score may be calculated by adding the discrimination scores for the number of times of stimulus presentation for each stimulus event. Alternatively, an arithmetic mean may be calculated.

(b-3) The results of averaging of the obtained discrimination scores for each stimulus types (including both the target and the non-target) are compiled as a data arrangement of the target stimulus types×test stimulus (see FIG. 4). The discrimination scores in each game have greater values as the similarity to the brain waves with respect to the target stimulus increases. Accordingly, even in the case of a non-target stimulus, the discrimination score value becomes large if the similarity to the brain waves with respect to the target stimulus is high. Thus, the discrimination scores herein reflect the similarity between the stimulus types.

(b-4) In the present embodiment, in order to apply a dimensional compression technique, a physical distance between stimuli is calculated based on the discrimination scores reflecting the similarity between the stimuli. Specifically, Euclidean distances are calculated, and the data arrangement of the target stimulus types×test stimuli is converted into a triangular matrix. The expression indicated below (Expression 2) is a formula for calculating the Euclidean distance (ed) of a distance between an individual i and an individual j; p is the number of test stimuli; and X is the discrimination scores of individual i and individual j.

$$ed_{ij} = \sqrt{\sum_{k=1}^{p} (x_{ik} - x_{jk})} , \qquad \text{[Expression 2]}$$

(b-5) Based on the obtained triangular matrix and using a multivariate analysis method such as multidimensional scaling or principal component analysis, the stimulus types are plotted on dimensional coordinates. The multidimensional scaling is a visualization technique whereby, based on the Euclidean distance, the relationship of the stimulus types is constructed in a low-dimension. Specifically, coordinate values are determined so that the sum of the squares of the difference between a distance ($d_{ij}$, or more correctly, d with a hat placed on top) when the stimuli are arranged in a dimension and a distance between the stimuli ($d_{ij}$) is minimized. This can be determined from a stress value indicated by the following expression (Expression 3). Further, by looking at the square of the correlation of the Euclidean distance and the distance calculated from the relationship of the coordinate values calculated by multidimensional scaling, the adequacy of the obtained plot can be evaluated as an explanatory rate. According to the embodiment, the relationship between stimuli is visualized using multidimensional scaling, and the adequacy of the stimulus-to-stimulus similarity evaluation based on brain information is ensured by the explanatory rate.

$$\text{STRESS} = \sqrt{\frac{\sum\sum (d_{ij} - \hat{d}_{ij})^2}{\sum\sum d_{ij}^2}} \qquad \text{[Expression 3]}$$

(b-6) Display of Similarity Evaluation

The data after two-dimensional compression are plotted on a two-dimensional plane. When plotted for each object to be evaluated, the points of each object to be evaluated are plotted on the two-dimensional plane, whereby a two-dimensional distribution chart (brain information map) in which a plurality of objects to be evaluated are distributed can be created (see FIG. 5).

Figure 6:
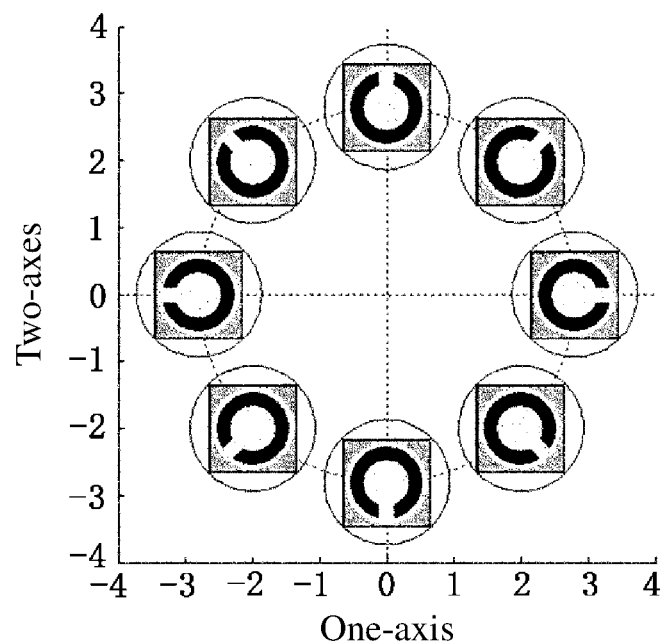
FIG. 6 illustrates theoretical values (A) and measured values (B) for describing the similarity evaluation results according to the first embodiment.
Figure 6:
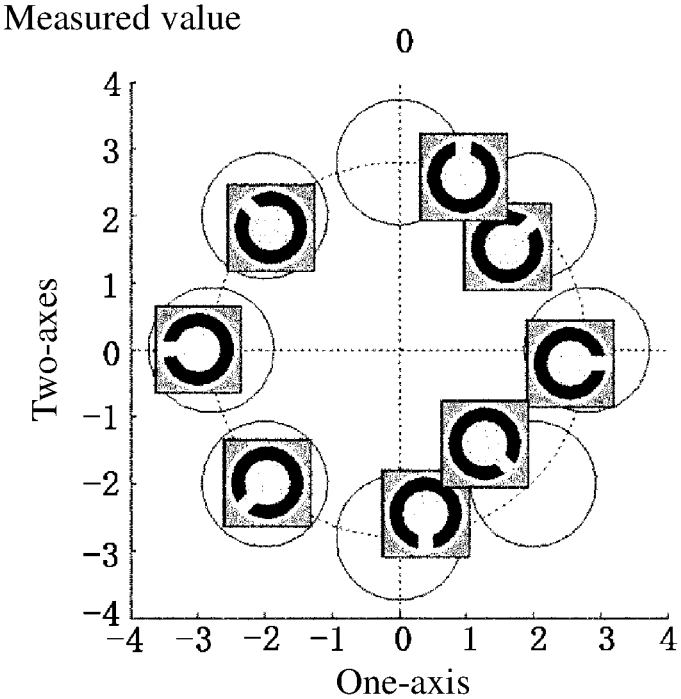

The effectiveness of the similarity evaluation according to the embodiment of the present invention is discussed below. FIG. 6 illustrates a comparison of the results of similarity evaluation. For verification, Landolt rings which are often used for ophthalmic visual acuity testing were used as visual stimuli. Specifically, eight kinds of Landolt rings (eight kinds with the gap facing different directions at 45° intervals) were presented to the subject successively, where the ring with the gap at a specific angle was defined as the target, and an experiment and data analysis were carried out according to the above-described procedure. As a result, it was confirmed that the Landolt rings with smaller angular differences were located closer to each other, resulting in an arrangement of an almost annular structure. Such arrangement has a very low probability of occurring by chance. FIG. 6(B) illustrates an analysis result based on the average values of discrimination scores with respect to the stimuli to seven subjects. In the case of a stimulus series using Landolt rings, analysis is possible when the angular differences in the gaps of the Landolt rings are converted into Euclidean distances. In fact, because the result was the annular structure, this proves that the external physical information was relatively accurately represented in the brain. FIG. 6(A) illustrates theoretical values corresponding to the measured values of FIG. 6(B).

While the effectiveness has been verified using the physical visual stimuli of Landolt rings, an actual product that serves as a visual stimulus object may include not only physical features but also psychological features affecting the conscious or the subconscious mind. It should be obvious that the similarity evaluation process according to the present invention will be useful for similarity evaluation including the conscious and the subconscious mind.

The examples indicated in the embodiment and the like are provided for assisting an understanding of the present invention, and are not to be taken as limiting the present invention to the embodiment.

INDUSTRIAL APPLICABILITY

The present invention provides a highly reliable and simple marketing research technique that may replace conventional questionnaire surveys.

REFERENCE SIGNS LIST

1 Stimulus presentation to subject
3 Electroencephalograph electrodes on subject
4 Brain wave amplifier
6 Computer

The invention claimed is:

1. An evaluation method for evaluating similarity of brain information with respect to a plurality of sensory stimuli, the evaluation method comprising dimensionally compressing brain wave data related to cognitive processing with respect to the plurality of sensory stimuli, and displaying a distribution of the stimuli on a two-dimensional plane or three-dimensionally, wherein the method comprises:

playing a game comprising presenting to a subject visual stimuli involving multiple evaluation objects, wherein one of the visual stimuli is a target and the other visual stimuli are non-targets and repeatedly presenting the target and non-targets pseudo randomly to the subject, wherein the subject counts the number of times the target is presented, and wherein brain waves of the subject are measured by an electroencephalogram;

generating a model equation set using a pattern recognition technique based on a waveform of the brain wave data received immediately after presentation of the visual stimulus so that discriminant scores generated from the model equation set have greater values for the target relative to the discriminant scores for the non-targets, and wherein the discriminant scores for the non-target having relatively greater visual stimulus similarity to the target are greater than the discriminant scores for the non-targets with relatively lower visual stimulus similarity to the target;

calculating a triangular matrix based on a data array of stimulus types times a number of games to indicate a difference in discriminant scores between different stimuli in terms of Euclidean distance;

applying multivariate analysis based on the triangular matrix; and evaluating the similarity by plotting the stimulus types on two-dimensional or three-dimensional coordinates based on the obtained triangular matrix.

2. The evaluation method according to claim 1, wherein the dimensional compression is based on a combination of multivariate analysis methods.

3. A non-transitory computer-readable medium containing instructions that when executed by the brain information similarity evaluation device cause the brain information similarity evaluation device to perform the method of claim 1.

4. A brain information similarity evaluation device comprising:

a stimulus presentation means configured to pseudo-randomly present to a subject a plurality of sensory stimuli as a plurality of stimulus events including a target and a non-target, each a plurality of times;

a brain wave measurement means configured to measure brain waves immediately after the stimulus presentation by the stimulus presentation means; and an evaluation processing means configured to evaluate visual stimulus similarity based on brain wave data and record electroencephalogram data related to the visual stimulus by generating a model equation set using pattern recognition technology to generate discriminant scores, wherein the discriminant scores generated from the model equation have greater values for the target relative to the discriminant scores of the non-target, and wherein discriminant scores for the nontarget having relatively greater visual stimulus similarity to the target are greater than the discriminant scores for the nontarget with relatively lower visual stimulus similarity to the target.

5. A brain information similarity evaluation system according to claim 4, wherein the evaluation processing means is further configured to obtain brain wave data while performing a cognitive task related to cognitive processing with respect to a plurality of sensory stimuli, dimensionally compress the brain wave data based on a combination of multivariate analysis methods, and display points corresponding to the stimuli on a two-dimensional plane or three-dimensionally.

\* \* \* \* \*